United States Patent [19]

VandenBerg

[11] Patent Number: Plant 7,469

[45] Date of Patent: Mar. 12, 1991

[54] CHRYSANTHEMUM PLANT NAMED MIRAMAR

[75] Inventor: Cornelis P. VandenBerg, Salinas, Calif.

[73] Assignee: Yoder Brothers, Inc., Barberton, Ohio

[21] Appl. No.: 415,920

[22] Filed: Oct. 2, 1989

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Miramar particularly characterized by its flat capitulum form; spoon daisy capitulum type; yellow ray floret color; diameter across face of capitulum of up to 14 cm at maturity when grown as a pinched disbudded pot mum; uniform nine week photoperiodic flowering response to short days; medium plant height when grown as a pinched pot mum; recommended both as disbud and spray pot mum; and semi-upright branching pattern.

3 Drawing Sheets

The present invention comprises a new and distinct cultivar of Chrysanthemum, botanically known as *Dendranthema grandiflora,* and referred to by the cultivar name Miramar.

Miramar, identified as 84-670003, was originated from a cross made by Cornelis P. VandenBerg in a controlled breeding program in Salinas, Calif., in 1984.

The female parent of Miramar was the cultivar identified as Pico, disclosed in U.S. Plant Pat. No. 6,772. The male parent of Miramar was an unnamed seedling identified as 82-366013.

Miramar was discovered and selected as one flowering plant within the progeny of the stated cross by Cornelis P. VandenBerg in April of 1985, in a controlled environment in Salinas, Calif.

The first act of asexual reproduction of Miramar was accomplished when vegetative cuttings were taken from the initial selection in June, 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Miramar are firmly fixed and are retained through successive generations of asexual reproduction.

Miramar has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Miramar, which, in combination, distinguish this Chrysanthemum as a new and distinct cultivar:

1. Flat capitulum form.
2. Spoon daisy capitulum type.
3. Yellow ray floret color.
4. Diameter across face of capitulum up to 14 cm at maturity, when grown as a pinched disbudded pot mum.

5. Uniform nine week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum in a 15 cm pot.
7. Recommended both as disbud and spray pot mum.
8. Branching pattern is semi-upright.

The accompanying photographic drawings show typical inflorescence and leaf characteristics of Miramar, with the colors being as nearly true as possible with illustrations of this type.

Sheet 1 is a color photograph of Miramar grown as a pinched disbudded pot mum grown in a 15 cm pot.

Sheet 2 is a black and white photograph of three views of the inflorescence of Miramar.

Sheet 3 is a black and white photograph showing the upper and under sides of the leaves of Miramar at three stages of development (mature, intermediate and immature).

Of the commercial cultivars known to the inventor, the most similar in comparison to Miramar is the female parent Pico. Reference is made to attached Chart A, which compares certain characteristics of Miramar to the same characteristics of Pico.

Similar traits are capitulum form and type, plant height and recommendation for both disbud and spray pot mum. The color of ray florets of Miramar is a darker yellow (RHS 9A) than that of Pico (RHS 3A). Miramar has a more upright branching pattern, a slightly larger flower diameter and a slower flowering response than Pico. Under certain conditions Pico exhibits some bracts in the center of the corolla of disc florets. Miramar does not exhibit this trait.

In the following description, color references are made to The Royal Horticultural Society Color Chart. The color values were determined on plant material grown as a pinched spray pot mum grown in a 15 cm pot in Salinas, Calif. on June 7, 1989.

Classification:

*Botanical.*—*Dendranthema grandiflora* cv Miramar.

*Commercial.*—Spoon daisy disbud and spray pot mum.

INFLORESCENCE

A. Capitulum:
*Form.*—Flat.
*Type.*—Spoon daisy.
*Diameter across face.*—Up to 14 cm at maturity.

B. Corolla of ray florets:
*color (general tonality from a distance of three meters).*—Yellow.
*Color (upper surface).*—9A to 9B.
*Color (under surface).*—9B.
*Shape.*—Base tubular. Distal portion open, flattened and spoon-like.

C. Corolla of disc florets:
*Color (mature).*—2A.
*Color (immature).*—144B to 144C.

D. Reproductive organs:
*Androecium.*—Present on disc florets only; moderate pollen.
*Gynoecium.*—Present on both ray and disc florets.

PLANT

A. General appearance:
*Height.*—Medium; 25 to 35 cm as a pinched spray pot mum with 0 to 7 long days after pinch prior to short days and 1 application of 2500 ppm B-9 SP.
*Branching pattern.*—Semi-upright.

B. Foliage:
*Color (upper surface).*—137A to 147A.
*Color (under surface).*—147B.
*Shape.*—Deeply lobed and slightly serrated. Foliage closest to the inflorescence has a tendency to twist and bend.

CHART A

COMPARISON OF MIRAMAR AND PICO

| CHARACTERISTIC | MIRAMAR | PICO |
|---|---|---|
| Ray Floret Color | Yellow | Yellow |
| Capitulum Form and Type | Flat<br>Spoon daisy | Flat<br>Spoon daisy |
| Branching Pattern | Semi-upright | Spreading and prolific |
| Diameter Across Face of Capitulum | Up to 14 cm | Up to 13 cm |
| Plant Height | Medium | Medium |
| Flowering Response Period | 9 weeks | 8 weeks |
| Recommended Use | Disbud and spray | Disbud and spray |

Comparisons Made of Plants Grown
As Pinched Spray Pot Mums
In Salinas, California

I claim:

1. A new and distinct Chrysanthemum plant named Miramar, as described and illustrated.

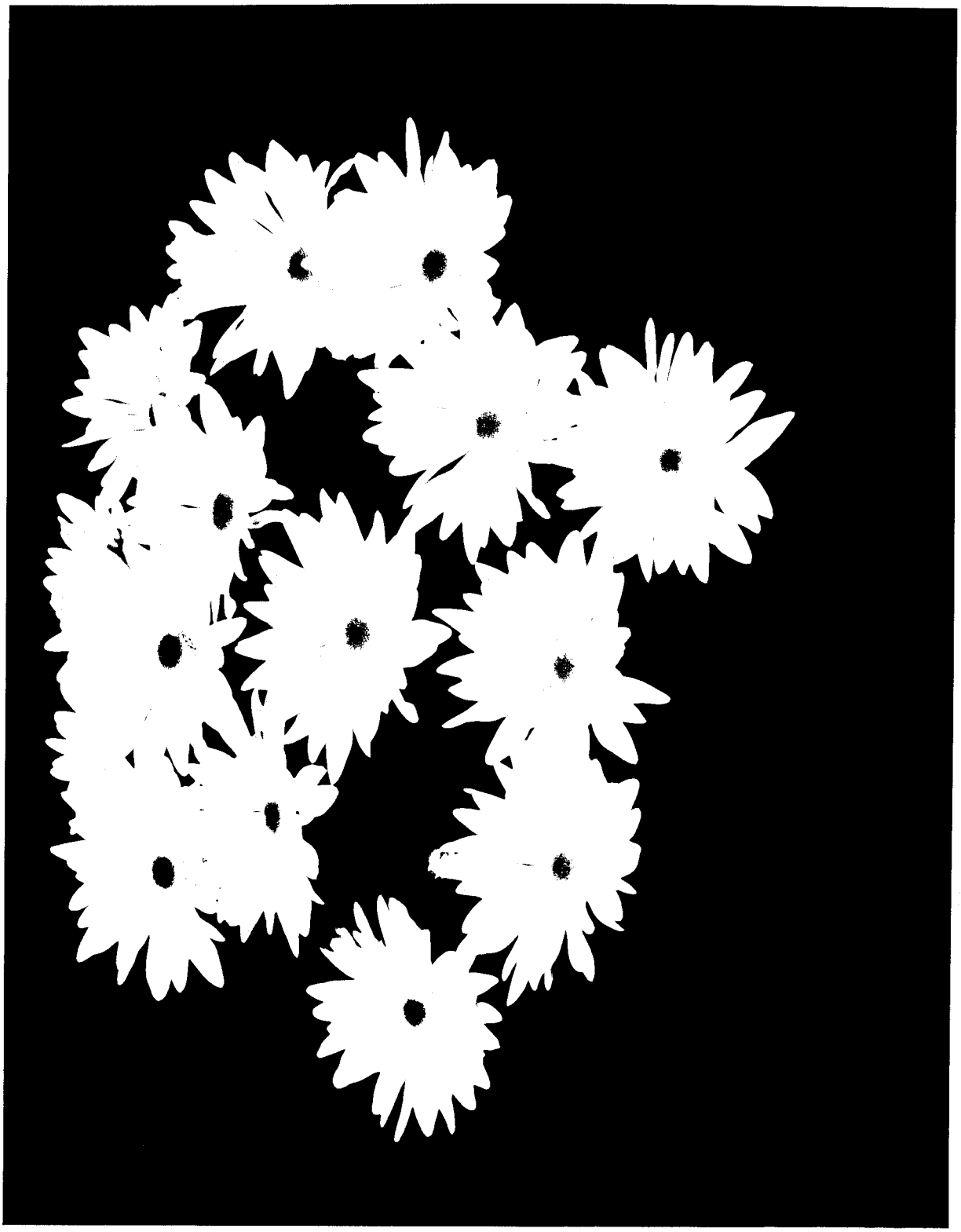

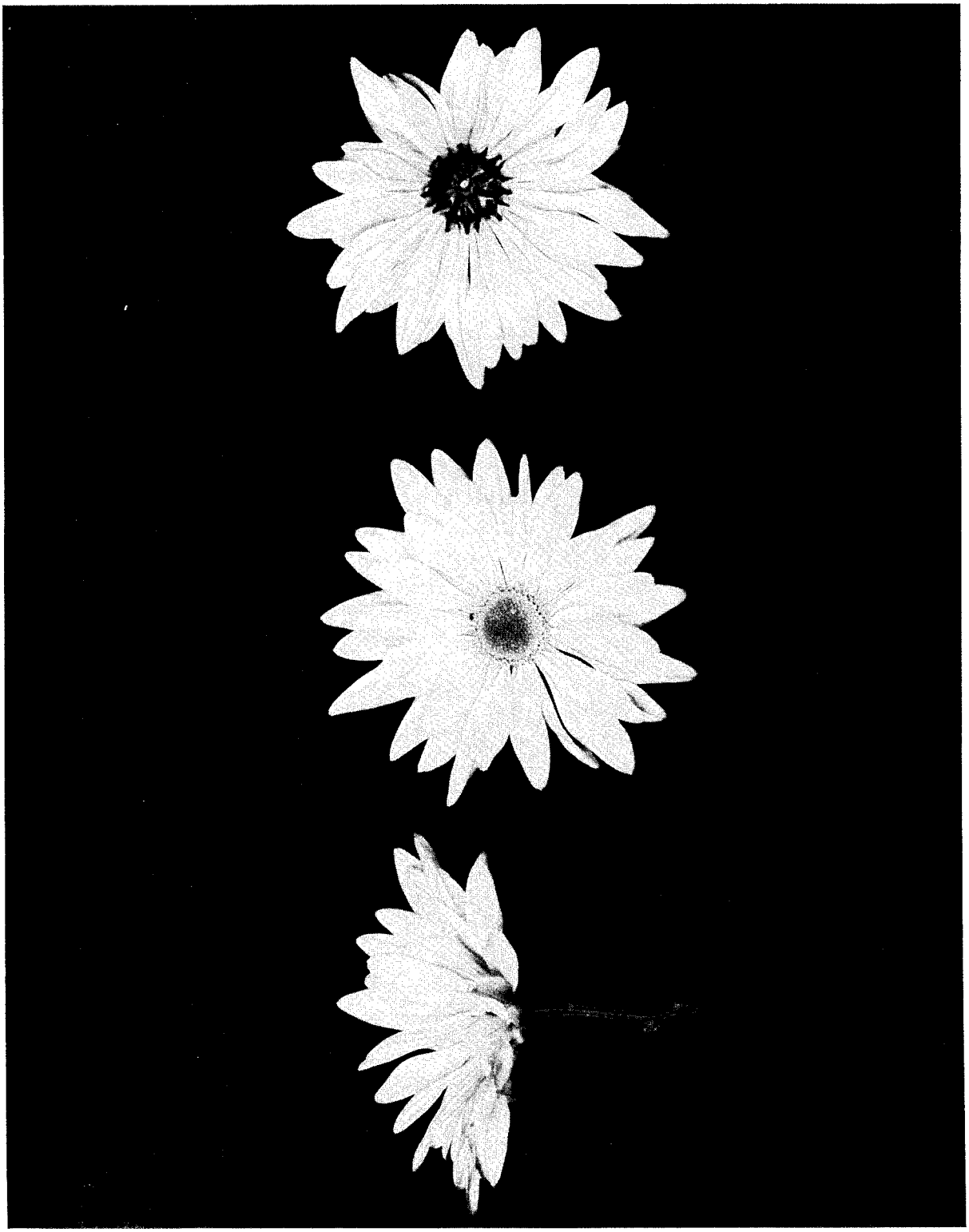

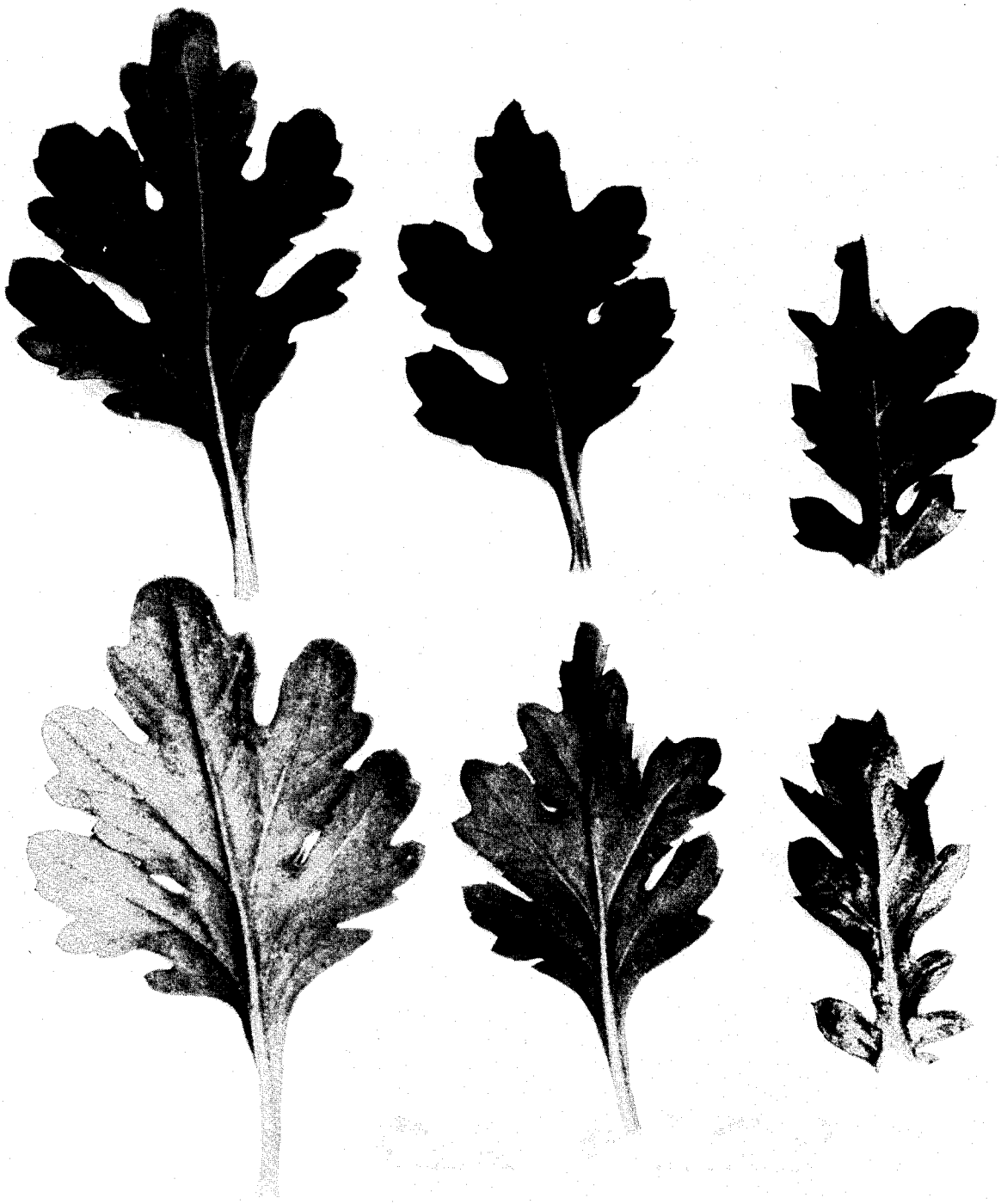

* * * * *